United States Patent [19]

Terhune

[11] Patent Number: 5,351,546
[45] Date of Patent: Oct. 4, 1994

[54] MONOCHROMATIC ULTRASONIC TRANSDUCER

[75] Inventor: James H. Terhune, San Jose, Calif.

[73] Assignee: General Electric Company, San Jose, Calif.

[21] Appl. No.: 964,998

[22] Filed: Oct. 22, 1992

[51] Int. Cl.⁵ .......................................... G01N 29/00
[52] U.S. Cl. ...................................... 73/642; 73/644; 73/632; 310/336
[58] Field of Search .................... 73/644, 642, 632; 310/336

[56] References Cited

U.S. PATENT DOCUMENTS

| | | | |
|---|---|---|---|
| 3,913,386 | 10/1975 | Saglio | 73/642 |
| 4,020,679 | 5/1977 | Barry | 73/644 |
| 4,366,406 | 12/1982 | Smith et al. | 73/632 |
| 4,870,972 | 10/1989 | Maerfeld et al. | 310/336 |
| 4,976,150 | 12/1990 | Deka | 73/644 |

FOREIGN PATENT DOCUMENTS

| | | |
|---|---|---|
| 0289383 | 11/1988 | European Pat. Off. |
| 0503977A2 | 9/1992 | European Pat. Off. |
| 3315649 | 6/1984 | Fed. Rep. of Germany |

OTHER PUBLICATIONS

J. & H. Krautkramer, Ultrasonic Testing of Materials, 4th Ed., Springer-Verlag (1990), pp. 18–23.

G. A. Georgiou et al., "The Application of the Geometrical Theory of Diffraction to Modelling Pulsed Ultrasonic Inspection: A System Model", Br. J. of NDT, vol. 31, No. 10, Oct. (1989), pp. 551–561.

Primary Examiner—Hezron E. Williams
Assistant Examiner—Nashmiya Ashraf
Attorney, Agent, or Firm—J. S. Beulick

[57] ABSTRACT

A transducer for generating or detecting ultrasonic energy of very narrow bandwidth which closely approximates a monochromatic source or detector has a gas gap of uniform dimensional width. The transducer employs standing ultrasonic waves generated, by multiple reflections and constructive interference, within the gap, effectively acting as a filter to pass only ultrasonic waves having a predetermined resonant frequency in response to impingement of broadband ultrasonic energy. This filtering effect enables the transducer to act as a source or detector of monochromatic ultrasound.

16 Claims, 3 Drawing Sheets

MONOCHROMATIC ULTRASONIC TRANSDUCER

FIELD OF THE INVENTION

This invention relates generally to non-destructive examination of material, such as metal, for voids, cracks and other defects that can be detrimental to the integrity of the material. Specifically, the invention relates to the ultrasonic inspection of nuclear and non-nuclear components at operating plants and facilities.

BACKGROUND OF THE INVENTION

The ultrasonic inspection of materials is often performed using refracted beams of sonic energy having frequencies in the range from 1 to 10 MHz. The means of producing such beams are well known in the art of ultrasonic transducer design, and either longitudinal or shear wave beams can be produced.

The waveform and associated frequency spectrum of a nominal 2.25-MHz impulse response for a conventional transducer are shown in FIGS. 1 and 2, respectively. The waveform of FIG. 1 has a damped oscillatory nature and a spectral content spread over a significant band of frequencies in the bell-shaped distribution shown in FIG. 2. The bandwidth is determined by the damping built into the transducer design, and either highly damped or lowly damped designs are available. Thus, either broadband or narrowband transducers can be obtained, depending on the application requirements.

If the transducer, rather than being pulsed, is instead driven with a sinusoidal excitation of finite duration, the resulting waveform can be derived from the convolution of the impulse response with the exciting function. A typical "tone burst" is shown in FIG. 3 for a nominal 2.25-MHz transducer. As can be seen in FIG. 3, the front-end of the waveform has an appreciable rise-time. The frequency spectrum of this waveform (see FIG. 4) is considerably narrower than that shown in FIG. 2, but is still far from monochromatic (i.e., possessing only a very narrow range or a single frequency), when compared with the spectrum of a conventional monochromatic source, such as that shown in FIG. 5.

In most standard applications of ultrasonics, the bandwidth is not critical and may be within predetermined broad limits. But for the purpose of detecting the size of flaws in a component of a nuclear reactor by means of scattered ultrasonic waves, narrow bandwidth can be an important factor in achieving accuracy. This implies that a monochromatic source of ultrasonic energy having a spectrum similar to that depicted in FIG. 5 would be a valuable tool, even though the spectral peak would be reduced.

SUMMARY OF THE INVENTION

The present invention is a transducer for generating (or detecting) ultrasonic energy of very narrow bandwidth which closely approximates a monochromatic source (or detector). This transducer enables detection and sizing of flaws in materials with much improved accuracy by exploiting the specific attributes of monochromatic ultrasonic radiation.

The ultrasonic transducer in accordance with the invention employs a unique and synergistic relationship between the properties of gases contained in a cell of uniform dimensional width. This relationship allows the transducer to select resonant ultrasonic energy from a relatively broadband source and transmit that energy without reflection or attenuation for the purpose of detection and/or sizing of material flaws.

To accomplish this feat, the transducer of the invention employs standing ultrasonic waves generated, by multiple reflections and constructive interference, within a uniform gas gap. The transducer effectively acts as a filter to pass only ultrasonic waves having a predetermined resonant frequency in response to impingement of broadband ultrasonic energy. This filtering effect enables the transducer to act as a source or detector of monochromatic ultrasound which is useful in nondestructive testing of material. The transducer utilizes the known properties of refraction wedges, or "shoes" in combination with gas gap transmission properties to generate monochromatic beams of both longitudinal and shear waves at specified refraction angles with predetermined beam angles.

One advantage of the invention is that it allows for meaningful continuous wave operation, or operation with long bursts of coherent waves, as opposed to the usual pulsed operation of standard ultrasonic transducers. This gives rise to the benefit that power is concentrated at, or near, a single frequency, instead of being spread over a broader range, thereby allowing for effective noise discrimination and enhanced signal-to-noise ratio. Tip diffraction from cracks can be optimized for frequency dependence, improving tip signal detection. Also the transducer can be "tuned" to predetermined frequencies that are most efficiently propagated in absorbing materials.

In accordance with a further aspect of the invention, temperature effects are controlled to ensure accurate frequency selection and to eliminate environmentally induced frequency drift.

Another advantageous feature of the ultrasonic transducer of the invention is that it substantially discriminates against shear waves and favors longitudinal (compressive) wave propagation, producing a more nearly pure ultrasonic field than is achievable using conventional transducers.

BRIEF DESCRIPTION OF THE DRAWINGS

These and other advantages of the invention will be better understood when the detailed description of the preferred embodiments of the invention is read in conjunction with the drawings, wherein.

DETAILED DESCRIPTION OF THE PREFERRED EMBODIMENTS

Figure 6:
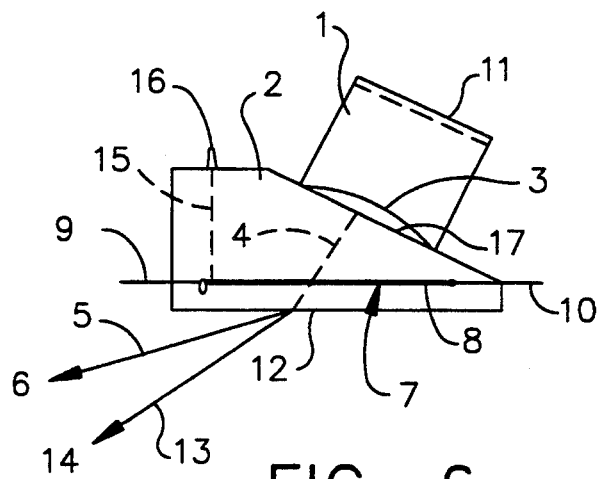
FIG. 6 is a schematic view of a monochromatic ultrasonic transducer in accordance with a preferred embodiment of the invention.

The monochromatic ultrasonic transducer in accordance with the preferred embodiment of the invention, as shown in FIG. 6, comprises a piezoelectric crystal 1 mounted on an inclined face of a block 2 (hereinafter "shoe") made of a material having an index of refraction substantially equal to the index of refraction of water. The preferred material is the acrylic resin available under the trade name LUCITE. A convergent lens 3 is arranged between piezoelectric crystal 1 and shoe 2.

When the transducer is being used as an ultrasonic transmitter, the piezoelectric crystal 1 is excited to oscillate by an electrical driving signal imposed at conventional crystal driving means 11 at its design frequency by external drive electronics (not shown in FIG. 6). In response to this electrical signal, the piezoelectric transducer produces an ultrasonic compressional wave (L-wave) beam. This beam is focused by convergent lens 3 to form a convergent ray bundle 4 propagating in shoe 2.

Shoe 2 is machined to form a very narrow disk-shaped gap 7 of uniform width therein. Although not required, it is desirable that gap 7 be parallel to outer shoe surface 12 to eliminate refraction effects. Gap 7 is filled with a gas or mixture of gases 8. The preferred gas is helium.

The gas 8 in gap 7 is maintained at a constant temperature by a heater rod 9. The heat output of heater rod 9 is monitored by a thermocouple 10. A controller (not shown in FIG. 6) is used to regulate the electric current supplied to the heater element in dependence on the signal received by the thermocouple. The controller is programmed in a conventional manner to maintain the gas at a constant elevated temperature.

In accordance with the invention, the sonic velocity and the gap width are selected such theft a single-mode standing wave is excited resonantly in the gap 7 at the desired frequency, allowing an ultrasonic beam 5 to penetrate the gap unperturbed to impinge upon the outer shoe surface 12.

During ultrasonic detection of cracks, outer shoe surface 12 is held in intimate contact with the surface of the material to be inspected. Typically, a gelatinous grease or couplant gel, such as ULTRAGEL, or water is used to ensure good contact.

The ultrasonic beam 5 is refracted at outer shoe surface 12 to propagate in the direction of the principal ray 6. In addition, the obliquely incident wave at outer shoe surface 12 is mode-converted to a shear-wave (S-wave) beam 13, which propagates in a direction 14 determined by the law of refraction. The refracted beams contain highly monochromatic energy due to the frequency selectivity of the gas gap.

The crystal face 17 makes a wedge angle $\theta$ with the outer shoe surface 12. Practitioners of ordinary skill in the art of ultrasonic detection will recognize that wedge angle $\theta$ determines the angle of refraction of the ultrasonic beam transmitted into the material to be inspected. An important special case is the one in which the angle $\theta$ is zero degrees, the so-called normal probe. The geometry of FIG. 6 is changed in an obvious way for this case, i.e., shoe 2 is formed as a block of rectangular cross section, so that face 17 is disposed parallel to outer shoe surface 12 and gap 7. This variation is included within the scope of the invention.

Figure 1:
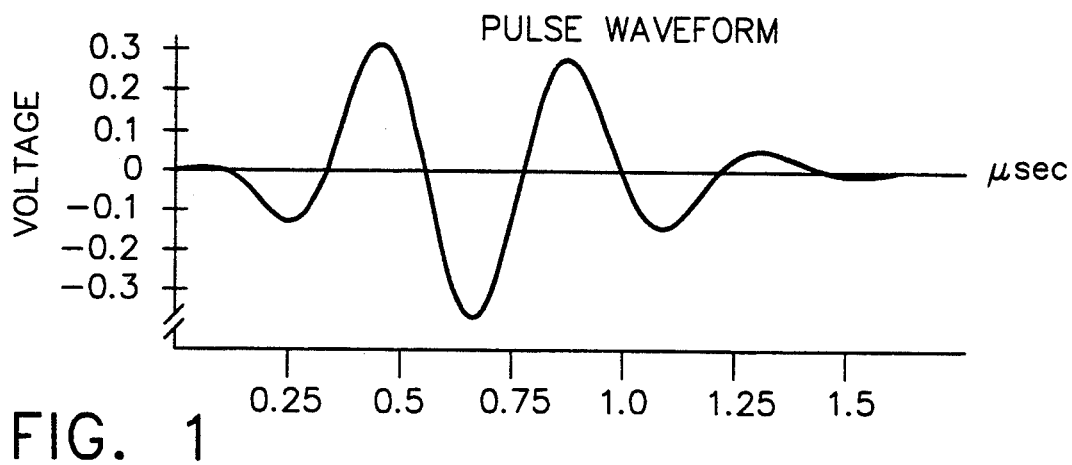
FIGS. 1 and 2 are graphs respectively depicting the waveform and frequency spectrum of the impulse response of a conventional transducer having a nominal frequency of 2.25 MHz.
Figure 2:
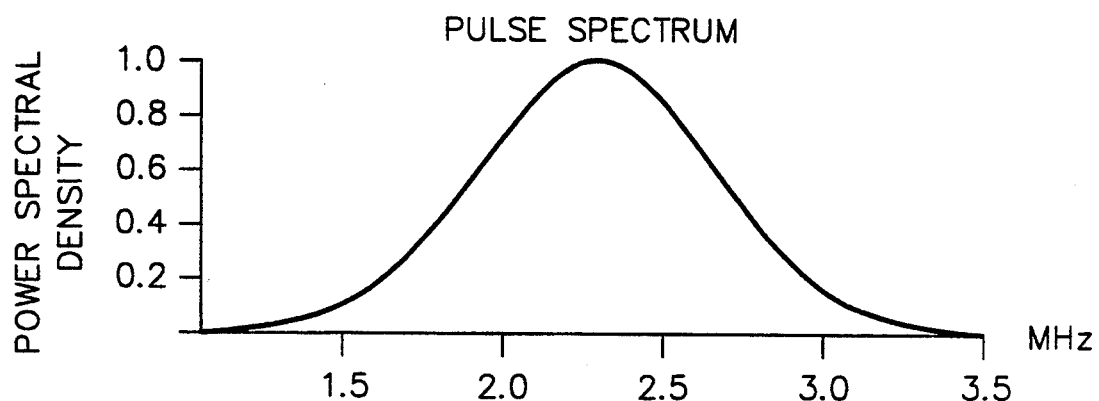
Figure 3:
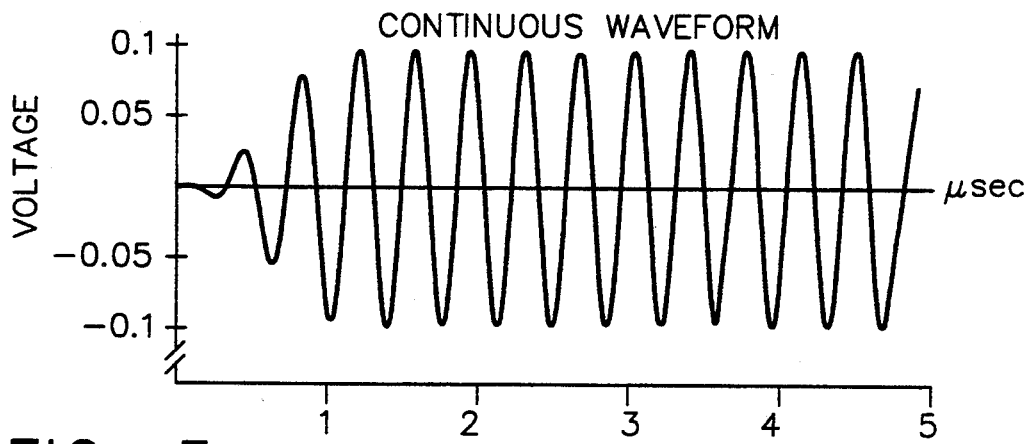
FIGS. 3 and 4 are graphs respectively depicting the waveform and frequency spectrum of the response of a conventional 2.25-MHz transducer to 2.684-MHz excitation.
Figure 4:
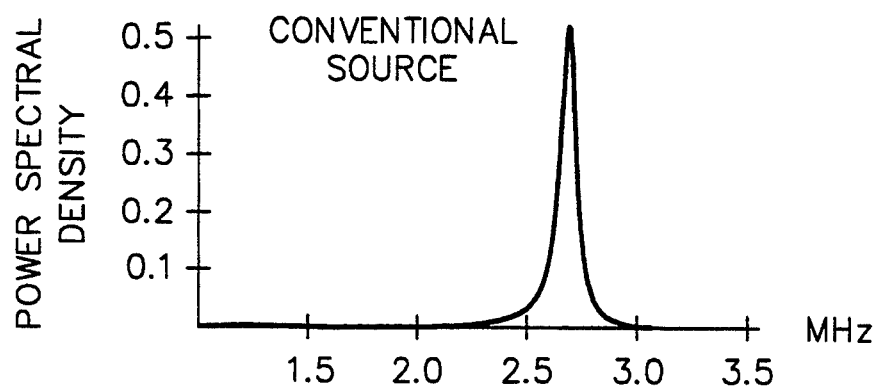
Figure 5:
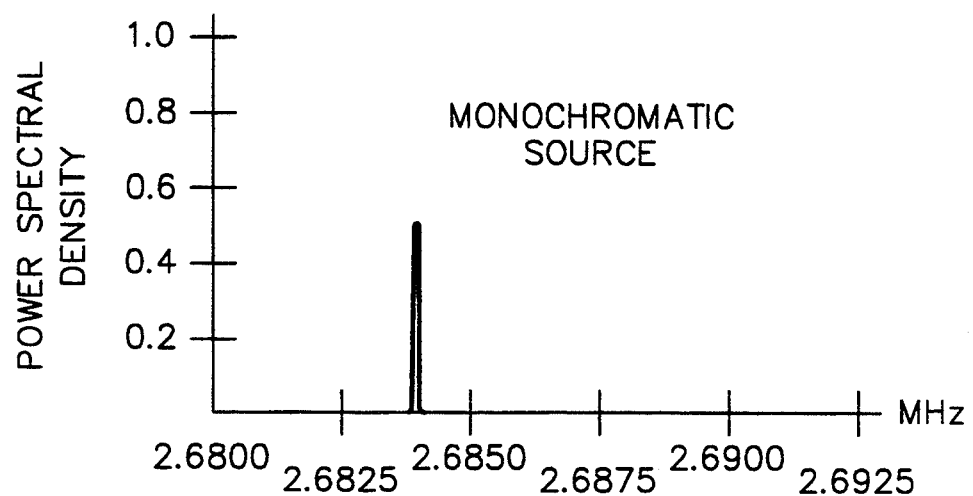
FIG. 5 is a graph depicting the frequency spectrum of a substantially monochromatic source of ultrasonic energy driven at 2.684 MHz.

It is found that the presence of the gas gap neither changes the angle of refraction of ultrasonic beam 5 nor diminishes the resonant energy incident upon the gap. The only function of the gap is to select a very narrow range of frequencies, such that the spectrum produced is essentially that shown in FIG. 5. Different wedge angles $\theta$ produce different angles of refraction, in accordance with Snell's law of refraction. Therefore, all permissible angles of refraction are included within the scope of the invention.

The use of a shoe in combination with both focused and unfocused crystal sources is conventional in the field of ultrasonic transducers. The novel feature of the present invention is the inclusion of a gas gap to produce essentially monochromatic ultrasonic beams 5 and 13 as the result of a synergistic interaction of the resonant interference effect in gap 7 with the refraction effect at the shoe/material interface 12.

The convergent ray bundle 4 incident on the gap 7 will be partially transmitted and partially reflected at the interfaces. This partial transmission and partial reflection will vary with the dimension of the gap 7, the type of gas therein and the frequency of the sound. For the proper frequency of sound within gas 8, the partial transmission at one interface of gap 7 constructively interferes with the partial reflection at the opposite interface of the gap, creating a standing wave in the gas filling the gap. This effect occurs when the gap width is a half-integral number of wavelengths. Thus, the dimensional width of gas gap 7 is critical. Typically, the gap width is in the range of 0.002 to 0.012 inch, depending on the frequency to be selected. For ease of understanding, the gap has not been depicted in FIG. 6 to scale.

The disk-shaped gas cell is out-gassed and back-filled, via a small port 15 and a pinch-off tube 16, with a pure gas or a gas mixture having a specific sonic velocity given by the equation:

$$c = \sqrt{\gamma RT/M}$$

where $\gamma$ is the ratio of specific heats for the gas or gas mixture; R is the gas constant; M is the molecular mass of the gas or gas mixture; and T is the absolute temperature of the gas or gas mixture. For wedge angle $\theta$ and relative index of refraction n (speed of sound in gas/longitudinal wave velocity in wedge material), the first-order resonant frequency $f_0$ is related to the gap width d in accordance with the formula:

$$f_0 = [c/(2d)] \sqrt{(1 - [n\sin(\theta)]^2)}$$

This equation is a slight function of temperature due to the gas sonic velocity dependence. Thus, the temperature of the gas in the gap must be controlled to assure accurate frequency selection and to eliminate frequency drift.

Higher-order resonant frequencies exist, which are the harmonics of the fundamental frequency given above. Similar arguments apply to those frequencies. A monochromatic ultrasonic transducer which selects one of the higher-order resonant frequencies may be built by proper selection of the gap width d. Such monochromatic ultrasonic transducers are also included within the scope of the present invention.

In accordance with the principles applied by the invention, the interference effect in the gap results in a frequency-sensitive energy transmission coefficient D given by the formula:

$$D = 1 / \left\{ 1 + \left[ \frac{(1/m - m)}{2} \sin\left(\pi \frac{f}{f_0}\right) \right]^2 \right\}$$

where m is the acoustical impedance ratio:

$$m = (\rho/Z) \sqrt{\gamma RT/M}$$

$\rho$ is the gas density and Z is the acoustical impedance of the wedge material.

Clearly, the sine-function in the expression for D vanishes at the resonant frequency, and the energy transmission coefficient is exactly unity at resonance, indicating that the gap is perfectly transparent at the resonant frequency. At other frequencies, D is very small in magnitude because m is very small. All other frequencies (except higher-order harmonics of $f_0$) are highly reflected at the first interface encountered by the acoustic wave. Thus, the gas gap acts as a very selective frequency filter, akin to an optical interference filter.

Since the expressions for $f_0$ and m contain the gas temperature T, the resonance filter of the invention is subject to temperature drifts due to environmental effects. To minimize this source of potential error, the LUCITE layer between the gap 7 and the shoe/material interface acts as an effective insulator to contain the heat generated in the gas by the heater element 9. The thermocouple 10 and controller maintain the temperature of the gas 8 inside gap 7 essentially constant, regardless of the temperature of the material of the component being examined. The gas temperature is elevated to a reasonable extent (typically 50°-80° C.) so that small temperature drifts and cycles are masked and controlled. Since helium is an excellent conductor of heat, the gas temperature in the gap is easily maintained at a uniform and constant value.

Figure 7:
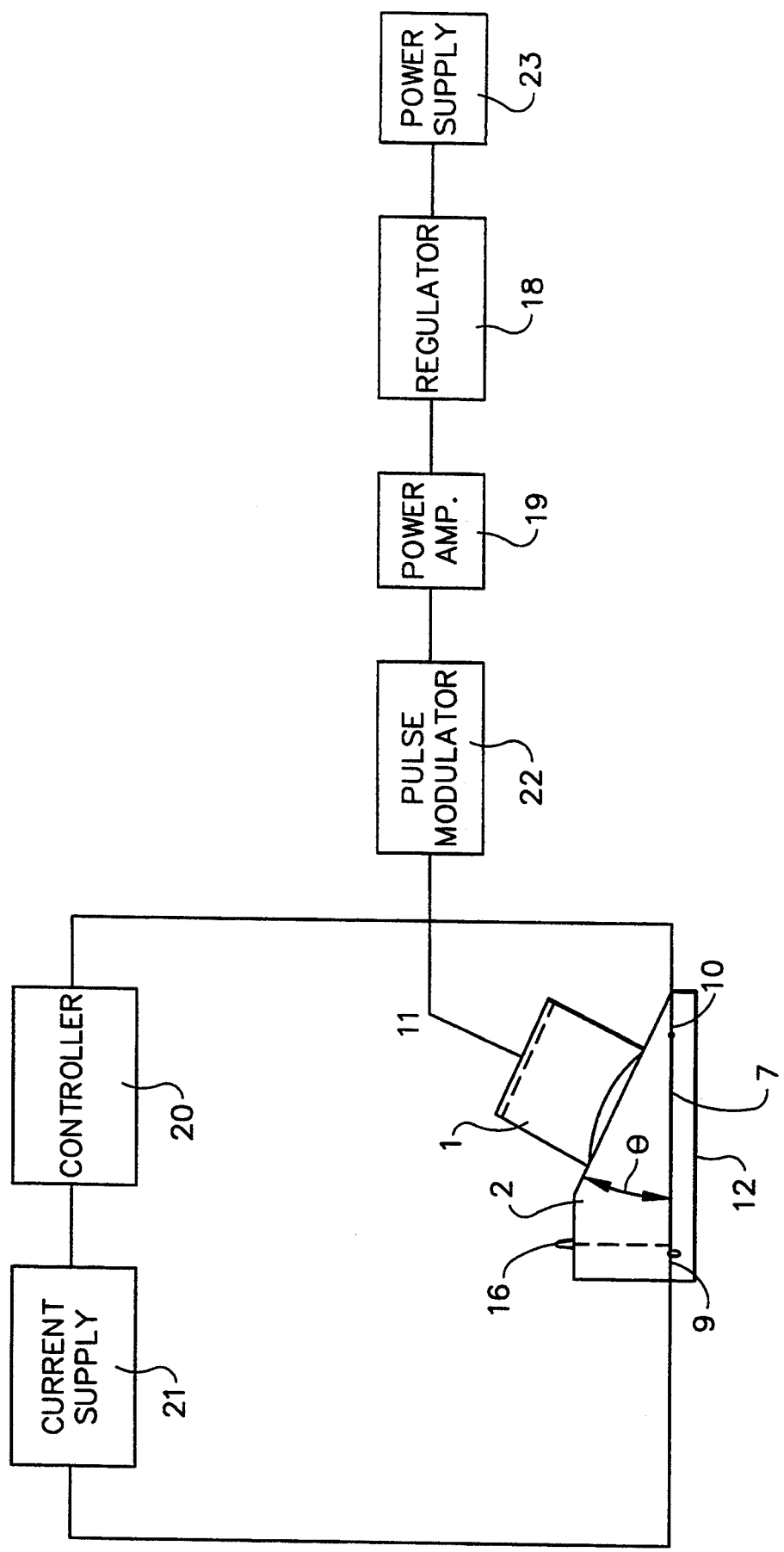
FIG. 7 is a block diagram of an ultrasonic source system incorporating the monochromatic ultrasonic transducer shown in FIG. 6.

When used as a transmitter, the monochromatic ultrasonic transducer in accordance with the preferred embodiment of the invention is incorporated in the ultrasonic source system depicted in FIG. 7. The description of elements in FIG. 7 bearing the same reference numerals as numerals used in FIG. 6 will not be repeated for the sake of brevity.

As previously described, the gas in gap 7 is heated by element 9 and the temperature of the heated gas is detected by thermocouple 10. Controller 20 monitors the signal received from thermocouple 10 and automatically adjusts the current supplied to element 9 by current supply 21 to maintain a constant gas temperature.

Piezoelectric crystal 1 is excited by the power amplifier 19, which in turn is powered by the regulated power supplied by power supply 23 via regulator 18. When thus excited, crystal 1 generates a continuous wave (CW) of relatively broadband L-wave ultrasound having a power spectrum of predetermined bandwidth, which is subsequently filtered by gas gap 7. Alternatively, crystal 1 can produce ultrasound in response to "tone bursts" produced repetitively by the action of a pulse modulator 22 (optional).

Care must be exercised in fabricating the gas cell to assure there are no leaks and that the gap has a uniform dimension. This is best done by numerically controlled machining of the cell on the surface of a first body made of LUCITE, followed by the joinder via appropriate means of a second body of LUCITE material to the first body, the joined bodies constituting the shoe in accordance with the invention. Cleaning and out-gassing assure that the helium back-fill gas is not contaminated to any significant degree.

The filtered source is not an energy-efficient source of monochromatic ultrasound, since a large fraction of the incident energy on the gap is non-resonant and reflected. However, if the piezoelectric crystal 1 is driven at a frequency close to the resonant frequency, efficiency is enhanced, especially in the case of CW excitation. Because the pulsed spectrum contains little energy at the resonant frequency, CW operation is the preferred mode.

The monochromatic ultrasonic transducer can be used as a detector, or receiver, of resonant energy, as well as a source. This is a consequence of the reciprocity law applicable to the ultrasonic field. Therefore, if the energy in the L-wave (or S-wave) beam depicted in FIG. 6 encounters a flaw in the material being inspected, some of the beam energy will be reflected or scattered at the resonant frequency. This signal can be readily detected using a transducer identical to the source of ultrasound shown in FIG. 6 and located appropriately.

In the CW mode, the reflection signal returned to the source is not a convenient means of detection. Therefore, coherent scattering by the flaw is the primary method of detection in this mode.

Refracted L-wave operation is a preferred mode of application for the monochromatic ultrasonic transducer of the invention. This is because the S-wave beam is very inefficient, resulting in low-level signals from flaws in the material being inspected. The S-wave sensitivity is also in a different direction than that for the L-wave, as indicated in FIG. 6 by arrows 6 and 14. Therefore, a further discrimination between modes exists, unless refractions result in S-waves entering the sensitivity cone of the L-waves. The presence of the shear-field is essentially a small background effect of little practical consequence, which is beneficial to certain types of materials inspections.

I claim:

1. An ultrasonic transducer comprising: piezoelectric means capable of transforming electrical energy into ultrasonic energy and transforming ultrasonic energy into electrical energy;

means for supplying continuous wave electrical energy having a power spectrum of predetermined bandwidth to said piezoelectric means;

solid medium means for propagating ultrasonic energy;

coupling means for allowing transmission of ultrasonic energy from said piezoelectric means to said solid medium means; and a gap of uniform width located inside said solid medium means, said gap being an open volume filled with fluid medium, said gap width and said fluid medium being such that said gap transmits therethrough only ultrasonic energy having a power spectrum of bandwidth narrower than said predetermined bandwidth and centered on a frequency of a standing wave produced in said fluid-filled gap.

2. The ultrasonic transducer as defined in claim 1, wherein said fluid medium is a gas medium.

3. The ultrasonic transducer as defined in claim 1, wherein said piezoelectric means comprises a piezoelectric crystal, said coupling means comprises a convergent lens and said solid medium means comprises a block of solid material having an index of refraction substantially equal to the index of refraction of water.

4. The ultrasonic transducer as defined in claim 2, further comprising means for heating said gas medium, means for detecting the temperature of said gas medium and means for controlling said heating means in dependence on the temperature detected by said detecting means.

5. The ultrasonic transducer as defined in claim 2, wherein said gap is a disk-shaped space machined into said solid medium means.

6. The ultrasonic transducer as defined in claim 2, further comprising means for filling said gap with said gas medium, said filling means being incorporated in said solid medium means.

7. The ultrasonic transducer as defined in claim 2, wherein said gas medium comprises helium.

8. The ultrasonic transducer as defined in claim 2, wherein said gap is positioned such that ultrasonic energy transmitted from said piezoelectric means via said coupling means is incident on an interface between said gap and said solid medium means.

9. An ultrasonic transducer comprising:
 a piezoelectric crystal;
 means for supplying continuous wave electrical energy having a power spectrum of predetermined bandwidth to said piezoelectric crystal;
 a solid medium for propagating ultrasonic energy;
 coupling means for allowing transmission of ultrasonic energy from said piezoelectric crystal to said solid medium; and
 a gap of uniform width located inside said solid medium, said gap being an open volume filled with fluid medium, said gap width and said fluid medium being such that said gap transmits therethrough only ultrasonic energy having a power spectrum of bandwidth narrower than said predetermined bandwidth and centered on a frequency of a standing wave produced in said fluid-filled gap.

10. The ultrasonic transducer as defined in claim 9, wherein said fluid medium is a gas medium.

11. The ultrasonic transducer as defined in claim 10, further comprising means for heating said gas medium, means for detecting the temperature of said gas medium and means for controlling said heating means in dependence on the temperature detected by said detecting means.

12. The ultrasonic transducer as defined in claim 9, wherein said coupling means comprises a convergent lens and said solid medium has an index of refraction substantially equal to the index of refraction of water.

13. The ultrasonic transducer as defined in claim 10, wherein said gas medium comprises helium.

14. The ultrasonic transducer as defined in claim 10, wherein said gap is positioned such that ultrasonic energy transmitted from said piezoelectric crystal via said coupling means is incident on an interface between said gap and said solid medium.

15. An ultrasonic transducer comprising:
 piezoelectric means capable of transforming electrical energy into ultrasonic energy and transforming ultrasonic energy into electrical energy;
 means for supplying continuous wave electrical energy having a peak amplitude at a predetermined frequency $f_0$ to said piezoelectric means;
 a block of material having a first planar interface across which ultrasonic energy can be transmitted between said piezoelectric means and said block and a second planar interface across which ultrasonic energy can be transmitted between a material to be inspected and said block, said first and second planar interfaces forming a predetermined angle $\theta$ therebetween, and said block of material having an index of refraction n; and
 a gap of uniform width d located inside said block and having an open volume filled with a fluid medium, said gap width d and said fluid medium being such that said gap transmits therethrough only ultrasonic energy having frequencies substantially equal to said predetermined frequency $f_0$.

16. The ultrasonic transducer as defined in claim 15, wherein said gap width d is related to said predetermined frequency $f_0$ by the formula:

$$f_0 = [c/(2d)] \sqrt{(1 - [n\sin(\theta)]^2)}$$

where c is the sonic velocity of said gas medium.

* * * * *